United States Patent
Verma et al.

(10) Patent No.: US 7,429,686 B2
(45) Date of Patent: *Sep. 30, 2008

(54) LOW PRESSURE OLEFIN RECOVERY PROCESS

(75) Inventors: Vijender K. Verma, Sugar Land, TX (US); Jichuan Hu, Sugar Land, TX (US)

(73) Assignee: Kellogg Brown & Root LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/780,682

(22) Filed: Jul. 20, 2007

(65) Prior Publication Data

US 2007/0260103 A1 Nov. 8, 2007

Related U.S. Application Data

(63) Continuation of application No. 10/884,659, filed on Jul. 2, 2004, now Pat. No. 7,294,749.

(51) Int. Cl.
*C07C 7/00* (2006.01)
(52) U.S. Cl. ...................................... 585/809
(58) Field of Classification Search ................ 585/809, 585/802, 800, 810; 208/24, 37
See application file for complete search history.

(56) References Cited

U.S. PATENT DOCUMENTS

| 5,453,559 A * | 9/1995 | Phillips et al. | 585/809 |
| 5,675,054 A * | 10/1997 | Manley et al. | 585/809 |
| 6,576,805 B2 * | 6/2003 | Keady et al. | 585/802 |
| 7,294,749 B2 * | 11/2007 | Verma et al. | 585/809 |

* cited by examiner

*Primary Examiner*—Walter D. Griffin
*Assistant Examiner*—Frank C Campanell
(74) *Attorney, Agent, or Firm*—KBR IP Legal

(57) ABSTRACT

A low-pressure olefins recovery process and plant are described. The feed gas is compressed and distilled at a primary distillation pressure. The overhead stream is chilled at a pressure less than 30 kg/cm2 (430 psia) to partially condense the overheads. The primary distillation tower is refluxed with at least a portion of the condensate. The overhead vapor is further chilled and partially condensed and the condensate is fed to a demethanizer. The remaining vapor is cooled in a cold section and the resultant liquid is phase-separated and expanded to provide refrigeration for the cold section. The expanded vapor from the cold section is recycled to the process gas compressor. The bottoms streams from the primary distillation zone and the demethanizer are fractionated into respective streams consisting essentially of ethylene, ethane, propylene, propane, C4's, and C5+.

13 Claims, 11 Drawing Sheets

LOW PRESSURE OLEFIN RECOVERY PROCESS

CROSS-REFERENCE TO RELATED APPLICATIONS

This application is a continuation of U.S. patent application Ser. No. 10/884,659, filed on Jul. 2, 2004, now U.S. Pat. No. 7,294,749 which is incorporated by reference herein.

FIELD

The present embodiments relate to an improved olefin recovery process, and more particularly to an olefin recovery process employing a low pressure front end distillation with a low pressure chilling train, a low pressure deethanizer and a low pressure demethanizer, to minimize the number of pieces of equipment that are needed to recover the olefins and to reduce the capital cost of the equipment.

BACKGROUND

Olefins are produced in a feed gas that originates from catalytic reactors and/or thermal cracking furnaces that are well known in the art, such as, for example, the SUPERFLEX™ process of Kellogg Brown & Root LLC, the catalytic process for cracking methanol, the deep catalytic cracking process, FCC reactors, and the like. The olefin containing feed gas must be processed to separate and recover the olefins from various amounts of other gases, which can include hydrogen, methane, ethane, propane, butanes, and pentanes-and-heavier hydrocarbons. The feed gas can also include contaminants such as carbon dioxide, acetylene, arsenic, mercury, carbonyl sulfide, nitrogen oxides, oxygen, and the like, which must generally be removed or treated.

In some conventional olefin recovery processes, the feed gas is compressed and fractionated in a front-end, heat-pumped deethanizer or depropanizer, employing relatively high pressures on the order of 400-500 psia in the case of the front end deethanizer and 400-600 psia in the case of the front end depropanizer. Schematic diagrams showing these prior art olefin recovery schemes are illustrated in FIGS. 1 and 2. Front-end demethanizer processes have also been used, employing pressures of 500-600 psia. High pressures are required in these olefin recovery schemes to obtain high ethylene/propylene recoveries. These relatively high pressures typically require four compressor stages, and an expander-recompressor is employed around the cold section refrigeration system. The high pressure of the equipment and the number of pieces of equipment increases the capital cost of the equipment. It would be desirable to reduce the number of pieces of equipment, as well as the cost.

In the processing of feed gases containing trace amounts of nitrogen oxides, such as, for example, in FCC effluent, there is also a potential safety hazard that must also be considered. A reactor is normally used to remove nitrogen oxides before the process gas is sent to the cold section, but leakage or upset or other malfunction can result in nitrogen oxides being present in the cold section. The presence of nitrogen oxide at temperatures below about 105° C. can result in the formation and accumulation of nitrated gums in the coldest cold box exchanger. Nitrated gums are unstable and can explode if thermally or mechanically shocked. Temperatures below 105° C. in the cold box should be avoided to minimize the possibility of nitrated gum formation.

One goal is to maximize ethylene/propylene recovery while at the same time minimizing energy consumption and other operating costs. Often, the lower temperatures required to reduce the loss of olefin in tail gas and/or hydrogen product streams will require additional power, creating a trade-off between power consumption and olefin losses. To maximize heat and refrigeration recovery, a relatively large number of heat exchangers may be employed. Furthermore, higher olefin recovery rates can necessitate the use of colder temperatures below the temperature at which nitrated gums can form in the cold box.

BRIEF DESCRIPTION OF THE DRAWINGS

The detailed description will be better understood in conjunction with the accompanying drawings as follows.

Figure 1:
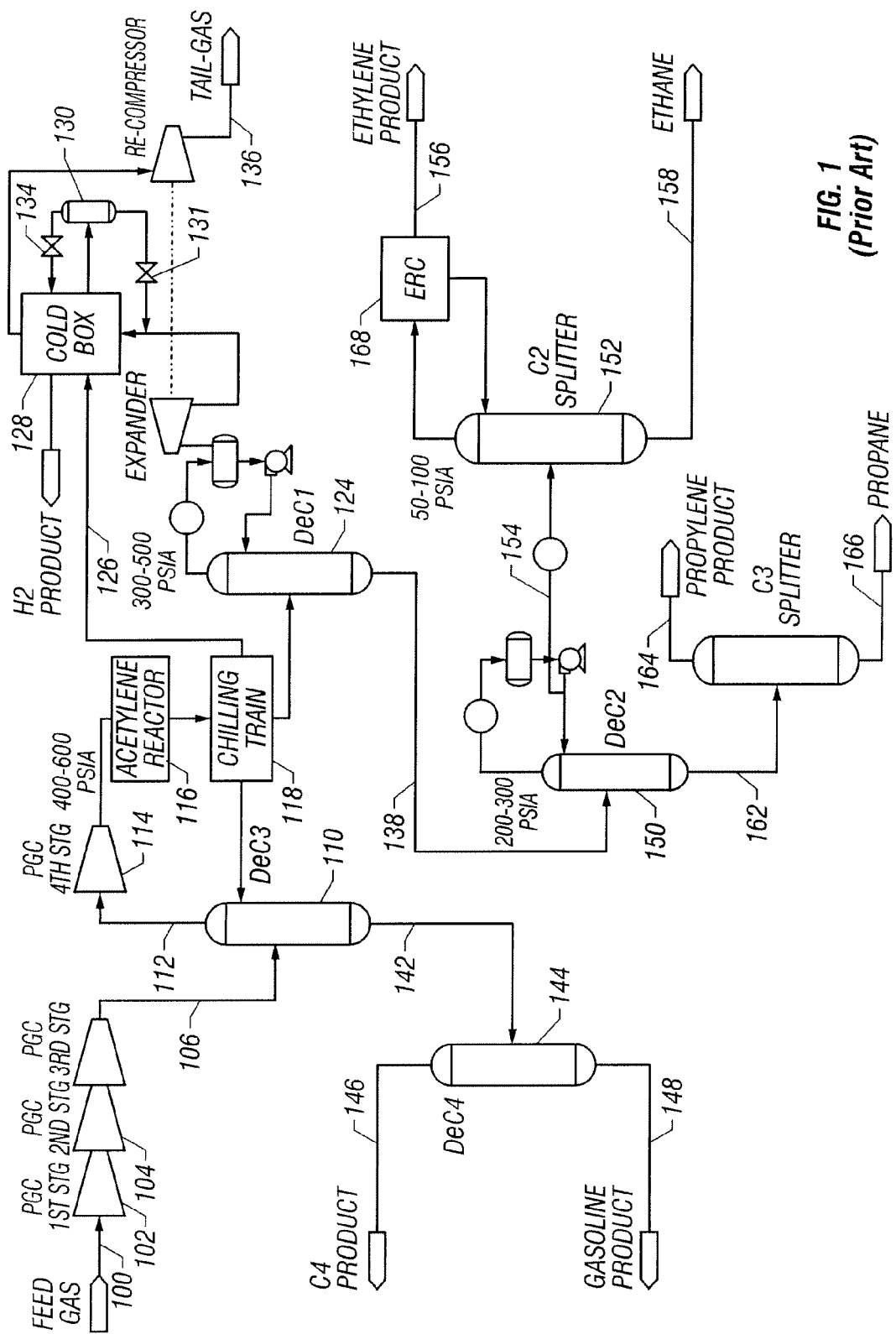
FIG. 1 (prior art) is a schematic flow diagram of a conventional high-pressure olefins recovery process with a front-end depropanizer.
Figure 2:
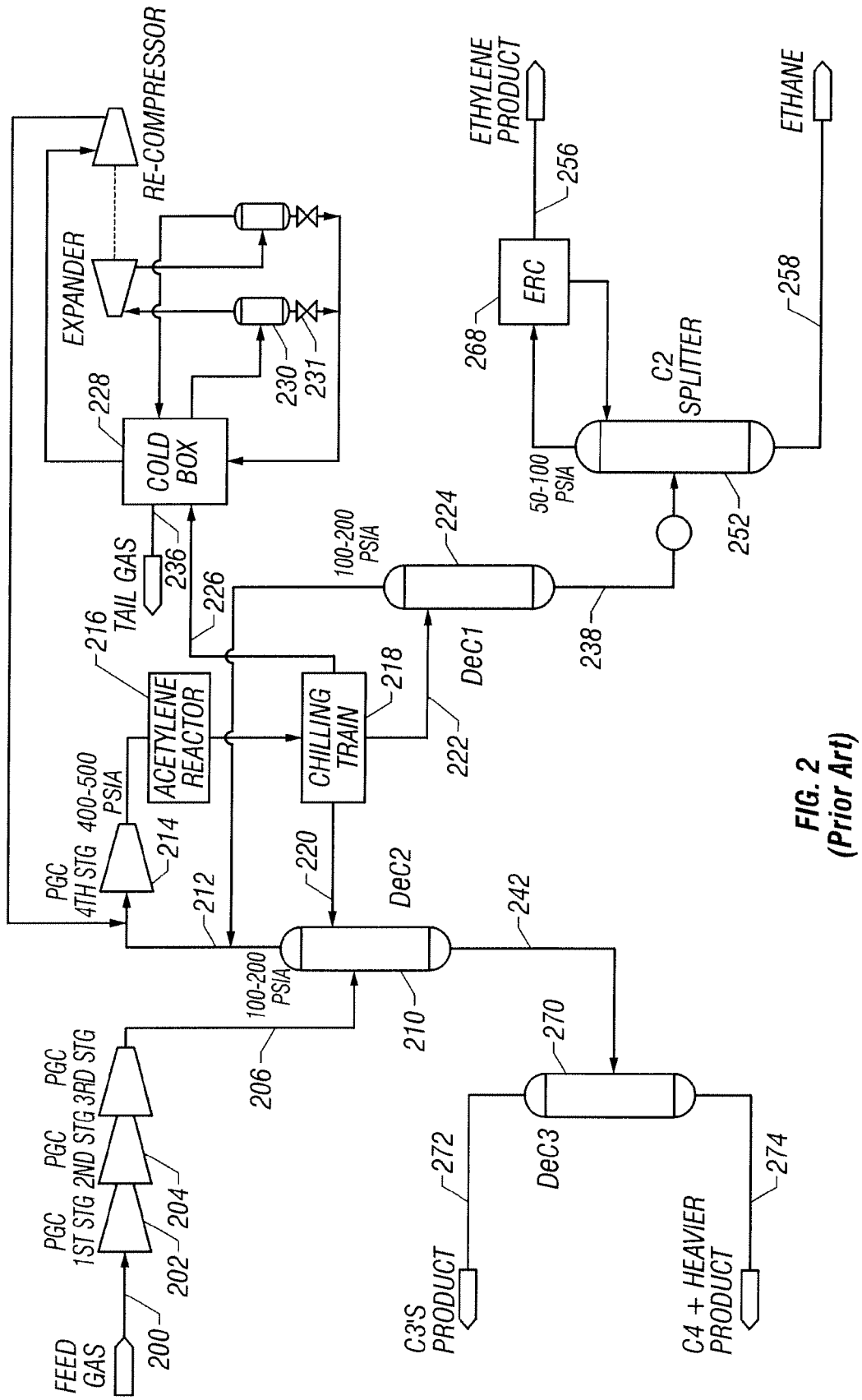
FIG. 2 (prior art) is a schematic flow diagram of a conventional high-pressure olefins recovery process with a front-end deethanizer.

The present embodiments are detailed below with reference to the listed Figures.

DETAILED DESCRIPTION OF THE EMBODIMENTS

Before explaining the present embodiments in detail, it is to be understood that the embodiments are not limited to the particular embodiments and that they can be practiced or carried out in various ways.

The present embodiments are olefin recovery processes that heat pumps the front-end distillation tower at a relatively low pressure, with good ethylene recovery and energy consumption. The process schemes result in fewer pieces of equipment, lower pressure ratings and lower capital costs.

In one aspect, an embodiment provides a process for recovering olefins from a feed stream. The process includes:

supplying the feed stream at a primary distillation pressure, including, if required, compressing the feed stream in at least one primary compression stage;

distilling the feed stream at the primary distillation pressure in a primary distillation zone to obtain a primary overhead vapor stream enriched in ethylene and one or more ethylene-lean bottoms streams;

chilling the primary overhead vapor stream at a pressure less than 30 kg/cm$^2$ (430 psia), preferably less than 28 kg/cm$^2$ (400 psia), in a first cooling stage to recover a first partial condensate stream and a first-stage vapor effluent;

refluxing the primary distillation zone with at least a portion of the first partial condensate stream;

further chilling the first-stage vapor effluent to recover at least a second partial condensate stream and a second-stage vapor effluent;

feeding the second partial condensate stream and any remaining portion of the first partial condensate stream to a demethanizer to recover a methane-rich overhead stream and a bottoms stream essentially free of methane and lighter components;

fractionating the bottoms streams from the primary distillation zone and the demethanizer into respective streams consisting essentially of hydrocarbons selected from the group consisting of ethylene, ethane, propylene, propane, $C_4$'s, $C_{5+}$ and combinations thereof, and further chilling the second-stage vapor effluent in a cold section and phase-separating the resulting mixed vapor-liquid stream in one or more stages to obtain additional condensate and a vapor tail gas stream essentially free of ethylene, wherein the additional condensate is vaporized at a relatively lower pressure to provide refrigeration for chilling and to form a low pressure recycle vapor stream.

The process can include passing the compressed feed stream and/or the primary overhead vapor stream in contact with a catalyst to remove contaminants such as acetylene, arsenic, mercury, carbonyl sulfide, nitrogen oxides, oxygen, combinations thereof, and the like.

The primary overhead vapor stream can be compressed in a secondary compression stage to a discharge pressure effective to provide reflux for the primary distillation zone. The primary distillation pressure can be from 7 to 21 kg/cm$^2$ (100 to 300 psia) and the discharge pressure from the secondary compression stage is preferably greater than the primary distillation pressure and less than 28 kg/cm$^2$ (400 psia). The discharge pressure from the secondary compression stage can be from 3.5 to 7 kg/cm$^2$ (50 to 100 psia) greater than the primary distillation pressure. One combination includes a primary distillation pressure from 7 to 11 kg/cm$^2$ (100 to 160 psia) and a secondary compression stage discharge pressure from 10.5 to 17.5 kg/cm$^2$ (150 to 250 psia).

The overhead stream from the demethanizer is preferably recycled into the primary overhead vapor stream upstream of the secondary compression stage. The demethanizer can consists essentially of an unrefluxed stripper column.

The low pressure recycle vapor stream from the cold section can be advantageously recycled into the feed stream upstream of at least one stage of the primary compression stage or stages. The process can include contacting a stream, selected from the mixed vapor-liquid stream, the vapor tail gas stream and a combination thereof, with a heavier hydrocarbon stream lean in ethylene to absorb residual ethylene from the stream into the heavier hydrocarbon which is recycled in the low pressure recycle vapor stream. The heavier hydrocarbon stream can consists essentially of liquid ethane, propane, or a combination thereof.

In one embodiment, the primary distillation zone comprises a depropanizer. In this embodiment, the process can include fractionating the bottoms stream from the depropanizer in a debutanizer to obtain respective streams consisting essentially of $C_4$'s and $C_5$'s and heavier hydrocarbons, and fractionating the bottoms stream from the demethanizer in a deethanizer, a $C_2$ splitter and a $C_3$ splitter to obtain respective streams consisting essentially of ethylene, ethane, propylene and propane. The deethanizer is preferably refluxed with a side draw from the $C_2$ splitter In an alternate embodiment, the primary distillation zone comprises a deethanizer and the process includes fractionating the bottoms stream from the deethanizer in a depropanizer, a $C_3$ splitter and a debutanizer to obtain respective streams consisting essentially of propylene, propane, $C_4$'s and $C_5$'s and heavier hydrocarbons, and fractionating the bottoms stream from the demethanizer in a $C_2$ splitter to obtain respective streams consisting essentially of ethylene and ethane.

In a further embodiment, the primary distillation zone comprises a depropanizer and a demethanizer, and the process includes fractionating a bottoms stream from the depropanizer in a debutanizer to obtain respective streams consisting essentially of $C_4$'s and $C_5$'s and heavier hydrocarbons, fractionating a bottoms stream from the deethanizer in a $C_3$ splitter to obtain respective streams consisting essentially of propylene and propane, and fractionating a bottoms stream from the demethanizer in a $C_2$ splitter to obtain respective streams consisting essentially of ethylene and ethane. In this embodiment, the process can include partially condensing overhead vapor from the depropanizer to form $C_4$-lean vapor and liquid streams, feeding the $C_4$-lean vapor stream to the deethanizer, and refluxing the depropanizer with the $C_4$-lean liquid stream.

Figure 3:
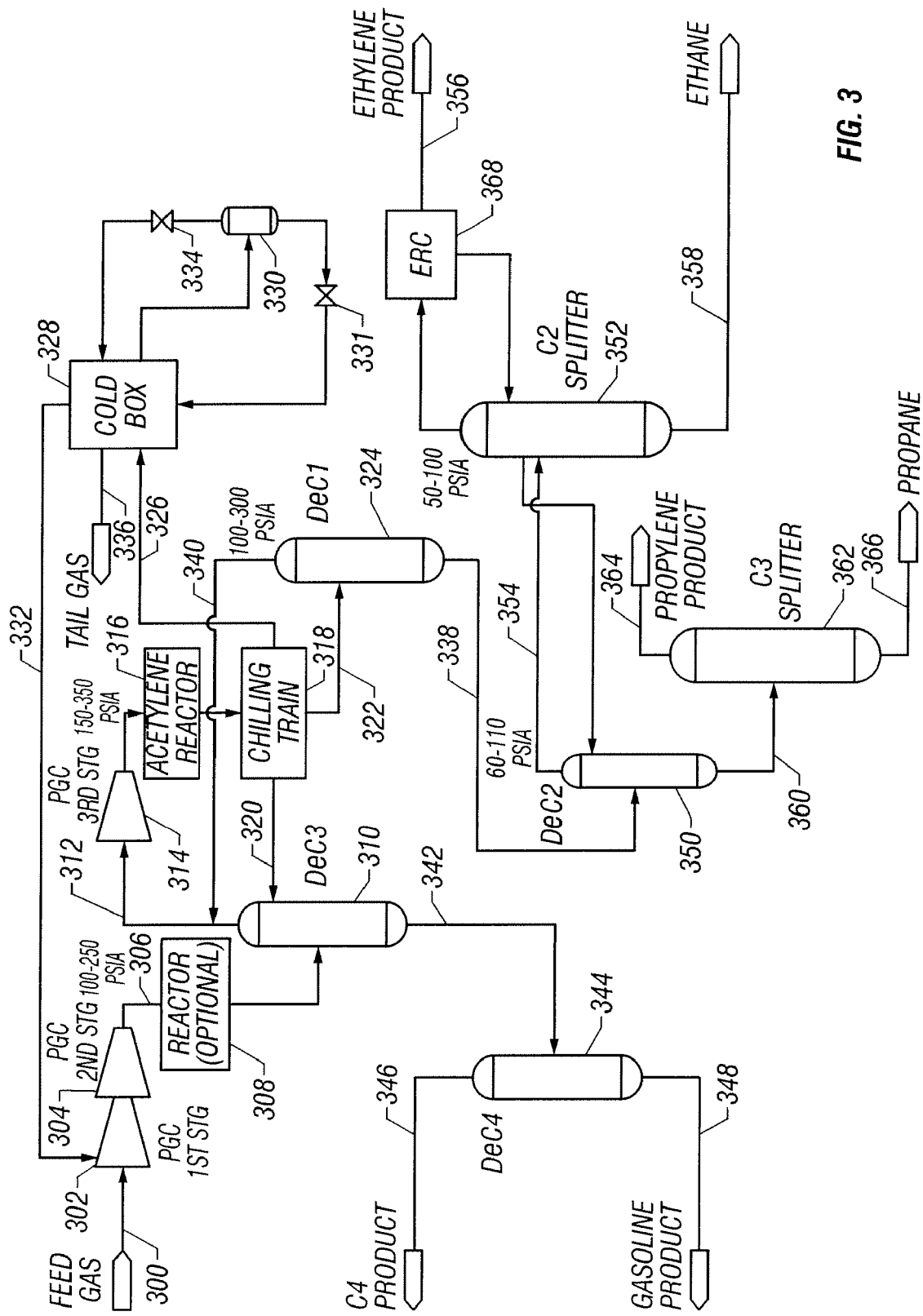
FIG. 3 is an example schematic flow diagram of a low-pressure olefins recovery process according to a present embodiment with a front-end depropanizer.

With reference to the figures, FIG. 3 is an example schematic flow diagram of a low-pressure olefins recovery process according to a present embodiment with a front-end depropanizer. In the front end depropanizer embodiment of FIG. 3, the embodiments supply an olefin-containing feed gas stream 300 to the suction of the first stage process gas compressor (PGC) 302 which operates in series with a second stage PGC 304 to produce an intermediate feed stream 306 at a pressure of 7 to 10.5 kg/cm$^2$ (100 to 250 psia), preferably 9.1 kg/cm$^2$ (130 psia). The feed stream 300 is typically washed in water and oil (not shown) to remove soot and heavy oil in a conventional manner, as well as to cool the stream 300 to ambient temperature or below, as required. Conventional interstage cooling (not shown) and liquid removal (not shown) can also be employed, if desired.

The intermediate feed stream 306 is optionally treated in conventional reactor unit 308, which can include an amine and/or caustic wash to remove acid gases and catalyst and/or adsorbent bed(s), such as impregnated carbon, nickel sulfide or the like, to remove arsenic, mercury, carbonyl sulfide, nitrogen oxides, oxygen or other contaminants. The unit 308 can include a conventional catalyst to react acetylene and a portion of methyl acetylene and propadiene (MAPD), and desiccants such as molecular sieve, alumina or the like, or a glycol system, to remove water. The gas can be further cooled before feeding to the front-end distillation tower 310.

The tower 310 can be a heat-pumped depropanizer, as exampled in the embodiment of FIG. 3, used to remove $C_4$'s and heavier hydrocarbons from the rest of the feed gas. The tower 310 is generally operated without an overhead condenser, using process condensate for reflux. The tower 310 overhead vapors in line 312 are compressed in the heat pump compressor stage 314 to a pressure of 10.5 to 24.5 kg/cm$^2$ (150 to 350 psia), preferably about 14 kg/cm$^2$ (200 psia), or as required by other process requirements, such as hydrogen delivery pressure, for example. The compressed overhead vapors can then be reacted over a conventional catalyst system 316 to remove acetylene and a portion of MAPD, if not removed in unit 308.

The compressed gas is successively cooled in chilling train 318 to the appropriate temperature, e.g. −18° C. (0° F.) in the case of the front-end depropanizer example, and the condensed liquid is phase separated. A portion of this liquid is returned via line 320 to reflux the tower 310. The remaining portion of the liquid is supplied via line 322 to demethanizer 324. The remaining vapor is further cooled as required, preferably to about −71° C. (−95° F.), and the condensed liquid is phase separated and supplied in line 322 to the demethanizer 324 together with the previously mentioned liquid from the earlier phase separation following the initial partial condensation. The remaining gases are supplied via line 326 to cold box 328 where they are further cooled to a temperature of −95° to −130° C. (−140° to −200° F.), preferably −115° C. (−175° F.), and phase separated in drum 330 and/or additional stages (not shown). The condensed liquid is expanded across Joule-Thompson valve 331 and vaporized at low pressure in the cold box 328 to provide the refrigeration required in the condensation step. After vaporization, the gas, which contains appreciable ethylene, is recycled via line 332 to the process gas compressor 302 to minimize ethylene losses. The vapor from the drum 330 is expanded across Joule-Thompson valve 334, passed through cold box 328 for recovery of refrigeration, and produced as an ethylene-lean tail gas 336 rich in methane and hydrogen.

The demethanizer 324 can be a low pressure stripping tower with few trays. The low pressure stripping tower with few trays produces a bottoms 338 that are essentially free of methane and lighter components. The overhead vapors 340 can be recycled, after reheating if required, to the suction of the heat pump stage 314 via line 312. Alternatively, the demethanizer 324 can be a refluxed tower (not shown) and the overhead methane-rich stream 340 can be further cooled for additional ethylene recovery and/or optionally expanded and used for fuel gas.

The bottoms stream 342 from the tower 310 can be supplied to a conventional debutanizer 344 that produces an overhead C$_4$ product 346 and a bottoms gasoline or C$_{5+}$ product stream 348.

The bottoms stream 338 from the demethanizer 324 is sent to deethanizer 350. The deethanizer 350 is preferably operated at a relatively low pressure, such as, for example, 4.2 to 7.7 kg/cm$^2$ (60 to 110 psia), for example about 5.0 kg/cm$^2$ (72 psia) at the top, and refluxed from the ethylene-ethane splitter (C$_2$ splitter) 352. In this configuration, the deethanizer 350 does not require a condenser that is conventional in other designs. The overhead vapor stream 354 is supplied to the C$_2$ splitter 352, which is operated to produce a high quality ethylene product stream 356 overhead and a bottoms stream 358 of essentially pure ethane. If desired, the deethanizer 350 and C$_2$ splitter 352 can be a mechanically integrated column as described in U.S. Pat. No. 6,077,985 to Stork, which is hereby incorporated herein by reference. The deethanizer bottoms stream 360, which can if desired include an MAPD reactor system (not shown), goes to a conventional C$_3$ splitter 362 for producing overhead propylene stream 364 and bottoms propane stream 366 as required.

The C$_2$ splitter 352 in this example can be heat pumped and coupled with ethylene refrigeration compressor 368, which can be a two-stage unit used to provide −73° F. (−100° F.) refrigeration used elsewhere in the process. Efficient use is made of the refrigeration available from various process streams and reboiler duties using conventional optimization schemes well known in the art to reduce the overall energy consumption in the process.

The C$_3$ splitter 362 can be either a low pressure, heat pumped tower or a standard cooling water-condensed tower as determined by economics. The propylene is used to provide refrigeration at about −40° C. (−40° F.) used elsewhere in the process.

The ethylene recovery from the FIG. 3 illustration is in the range of 98-99 percent, depending on the selected pressures and temperatures. The main ethylene losses are in the tail gas 336 leaving the −95° to −130° C. (−140° to −200° F.) drum 330.

Figure 4:
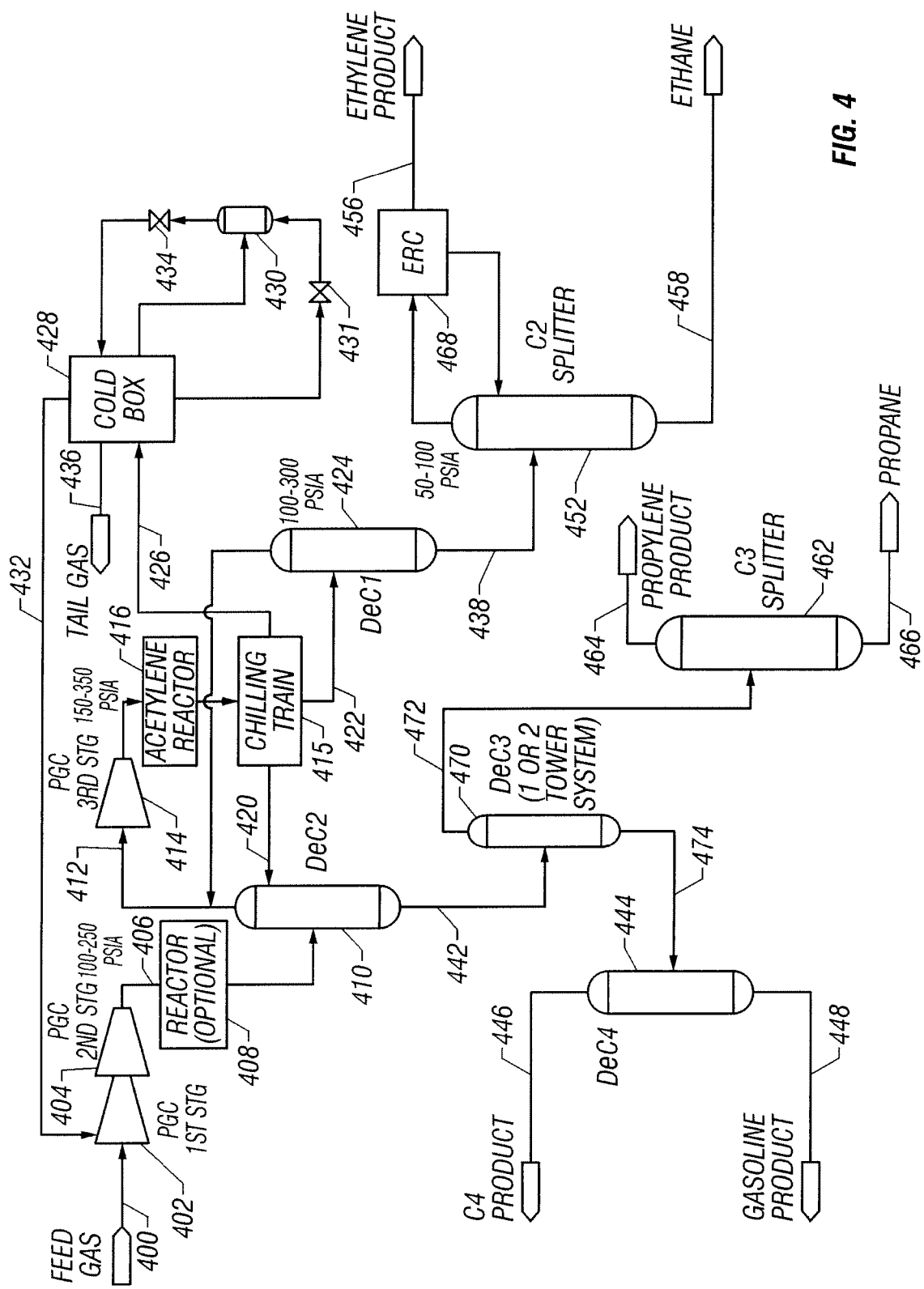
FIG. 4 is an example schematic flow diagram of a low-pressure olefins recovery process according to a present embodiment with a front-end deethanizer.

FIG. 4 is an example schematic flow diagram of a low-pressure olefins recovery process according to a present embodiment with a front-end deethanizer. FIG. 4 illustrates principles of the present embodiments in the context of a front-end deethanizer. In one embodiment, the tower 410 is a deethanizer and the bottoms stream 442, which is rich in propanes and heavier hydrocarbons, is supplied to depropanizer 470, which can be a single or dual tower system. The overheads stream 472 is supplied to the C$_3$ splitter 462, while the bottoms stream 474 is supplied to debutanizer 444 as in the FIG. 3 embodiment. Since the demethanizer 424 bottoms stream 438 is essentially free of propanes, it can be supplied directly to the C$_2$ splitter 452.

Figure 5:
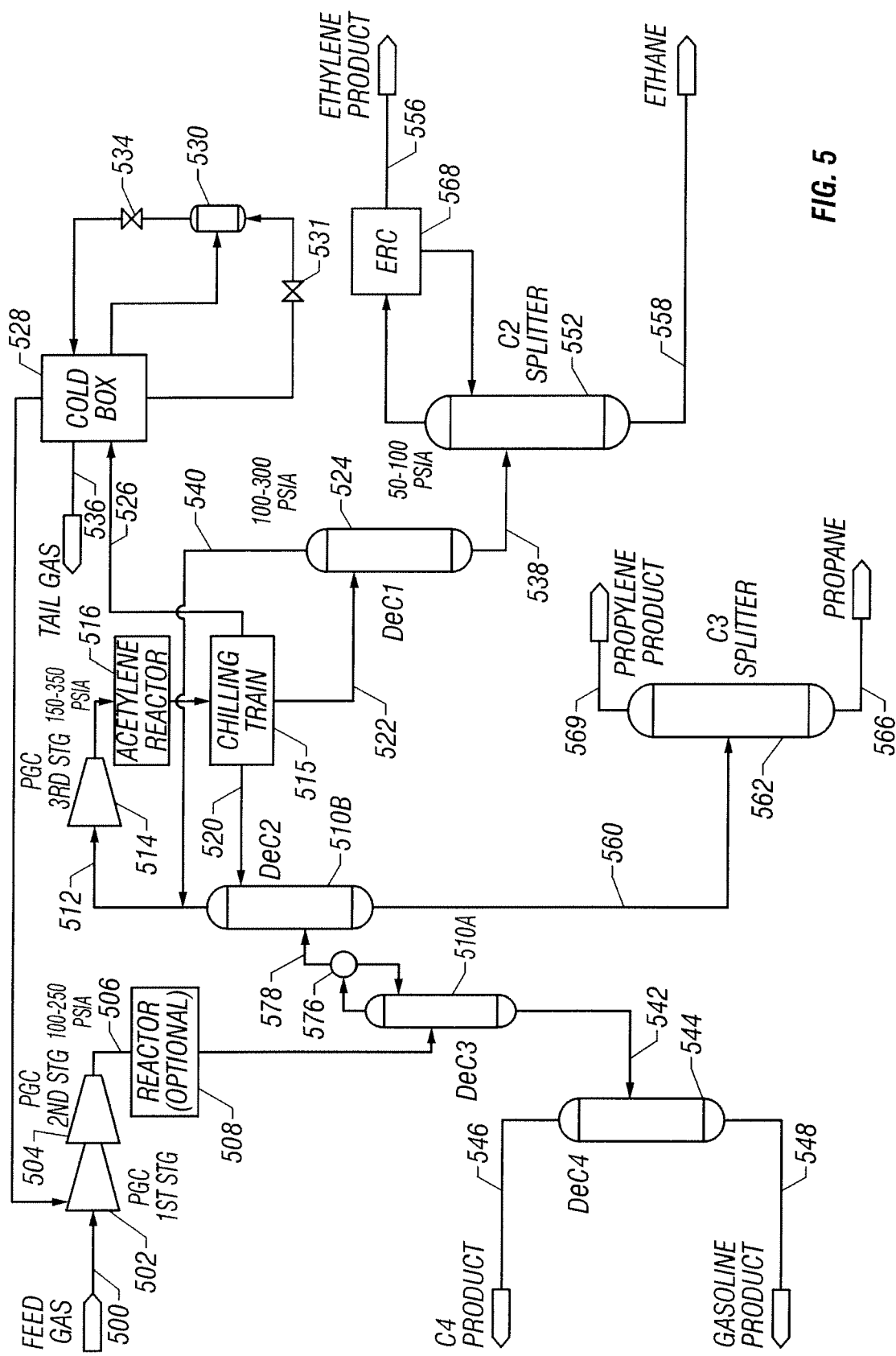
FIG. 5 is an example schematic flow diagram of a low-pressure olefins recovery process according to a present embodiment with a front-end depropanizer/deethanizer in series.

FIG. 5 is an example schematic flow diagram of a low-pressure olefins recovery process according to a present embodiment with a front-end depropanizer/deethanizer in series. FIG. 5 illustrates the principles of the present embodiments in the context of a front-end depropanizer 510A and deethanizer 510B operated in series. The depropanizer 510A can be operated with a conventional overhead reflux condenser (not shown) and reflux drum 576. Overhead vapor stream 578 is supplied to deethanizer 510B, which is heat pumped as in the FIG. 4 embodiment. The bottoms stream 542 from the depropanizer 510A is supplied to the debutanizer 544, while the bottoms stream 560 from the deethanizer 510B is supplied directly to the C$_3$ splitter 562. If desired, in this embodiment, a portion of the overhead vapor 512 from the deethanizer 510B and/or the vapor from the first cooling stage in the chilling train 518 can be exported as a dilute ethylene product stream.

Figure 6:
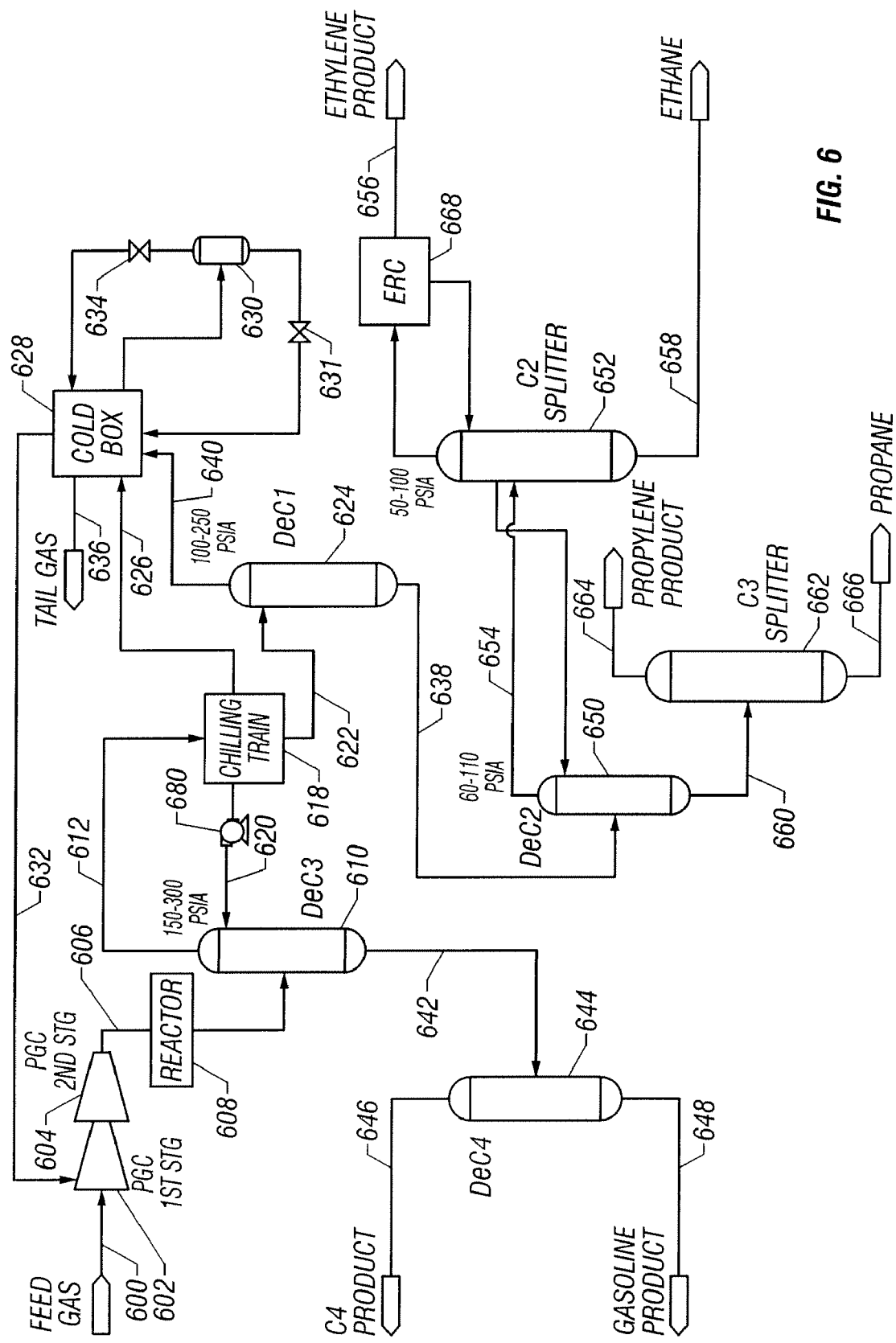
FIG. 6 is an example schematic flow diagram of a low-pressure olefins recovery process according to a present embodiment with a front-end depropanizer and a depropanizer reflux pump.

FIG. 6 is an example schematic flow diagram of a low-pressure olefins recovery process according to a present embodiment with a front-end depropanizer and a depropanizer reflux pump. FIG. 6 further illustrates the principles of the present embodiments in the context of a front-end depropanizer wherein the process gas compression is limited to two stages. In one embodiment, the discharge pressure of the second stage PGC 604 is about 10.5 to 24.5 kg/cm$^2$ (150 to 350 psia), more preferably about 12.6-14 kg/cm$^2$ (180-200 psia), and the overhead vapor 612 from the depropanizer tower 610 is supplied to the chilling train 618 essentially at the pressure of the tower 610, preferably about 10.5 to 11.2 kg/cm$^2$ (150 to 160 psia), especially about 10.85 kg/cm$^2$ (155 psia), without further compression. A reflux pump 680 is used to return the liquid stream 620 recovered from the chilling train 618 to the tower 610. The overhead vapor stream 640 from the demethanizer 624, which is not at a high enough pressure to be introduced into the depropanizer overhead stream 612, is instead heated in (or outside) the cold box 628 to recover refrigeration and recycled in line 632 to the suction of the first process gas compressor 602. This embodiment has the advantage of eliminating the need for a third process gas compressor stage required for heat pumping the tower 610 in the other embodiments.

Figure 7:
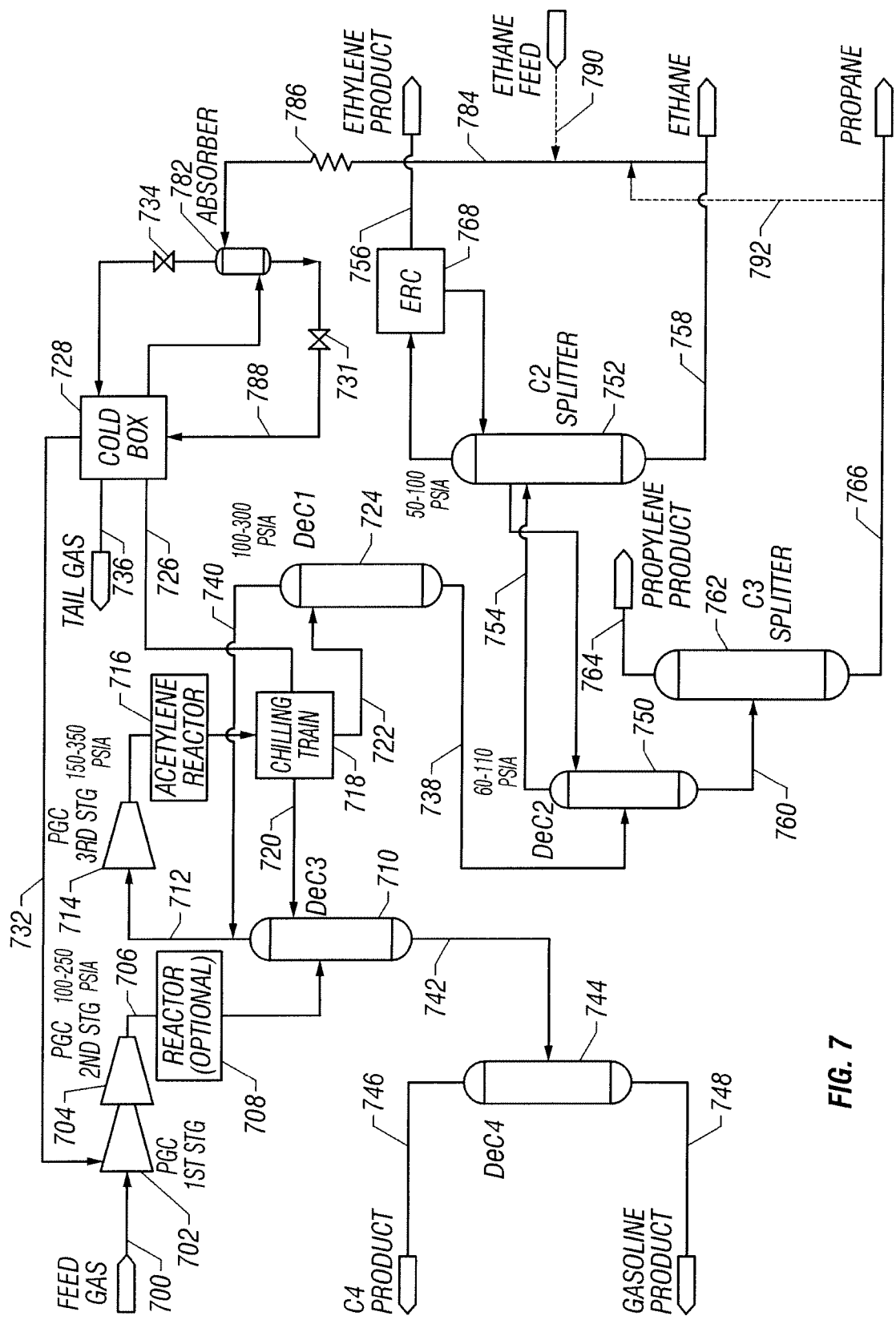
FIG. 7 is an example schematic flow diagram of a low-pressure olefins recovery process according to a present embodiment with a front-end depropanizer and an ethylene absorber.

FIG. 7 is an example schematic flow diagram of a low-pressure olefins recovery process according to a present embodiment with a front-end depropanizer and an ethylene absorber. The embodiment of FIG. 7 uses a front-end depropanizer with an ethylene absorber 782 to further reduce ethylene losses in tail gas stream 736. Ethylene absorber 782 is preferably a simple tower without a condenser or reboiler used in place of the separation drum 330 in FIG. 3. Ethane from line 758 (or from can be supplied via line 784, cooled in exchanger unit 786 and introduced as a wash liquid to the top of the ethylene absorber 782, at about the same pressure and temperature as the absorber 782, e.g. 14 kg/cm$^2$ (200 psia) and −95° C. (−140° F.). The ethane-ethylene liquid from the absorber 782 is collected in line 788 and recycled to the cold box 728, line 732 and process gas compressor 702. Alternatively, the ethane feedstock via line 790, if sufficiently pure or after being appropriately purified, or propane product via line 792, is used as the wash liquid. Using this embodiment, ethylene recoveries of 99 percent and higher are achieved, preferably at least 99.8 percent, while at the same time avoiding the use of extremely low temperatures. The ethylene absorber 782 is not limited to use with the front-end depropanizer scheme of FIG. 7, and can be utilized with any of the embodiments of FIGS. 3-6 in place of the cold box separator drum.

The embodiments achieve a reduction in the number of pieces of equipment that are used in the process, and thus concomitantly reduce the capital cost. For example, only two or three stages of process gas compression are used, compared to four or more in the conventional high-pressure prior art process. By operating a heat pumped, low-pressure initial distillation tower, the condenser and reflux drums and pumps are generally eliminated, and the tower has a relatively low number of trays. By coupling the deethanizer and C$_2$ splitter in the embodiment of FIG. 3, a condenser and reflux drum are eliminated and the C$_2$ splitter reboiler duty is significantly reduced, while the C$_2$ splitter condenser duty increases only slightly. By using the ethylene absorber in the FIG. 7 embodiment, the process can avoid nitrated gum formation temperatures while still maintaining high ethylene recovery and low power consumption. Very few heat exchangers are needed in the present process, yet it recovers refrigeration efficiently. If desired, the final pressure profile can be adjusted to eliminate pumps for the depropanizer bottoms, the demethanizer bottoms and the deethanizer bottoms, and no reflux pumps are required for the depropanizer, deethanizer, demethanizer and C$_2$ splitter. Also, waste quench water heat can be used for reboiling the depropanizer, saving steam costs. Furthermore, by operating at relatively low pressures, the present invention avoids the need to use a coupled expander-recompressor (or expander-generator) to recover compression around the cold box as in prior art olefin recovery schemes that operated at high pressure.

EXAMPLE 1

Figure 8A:
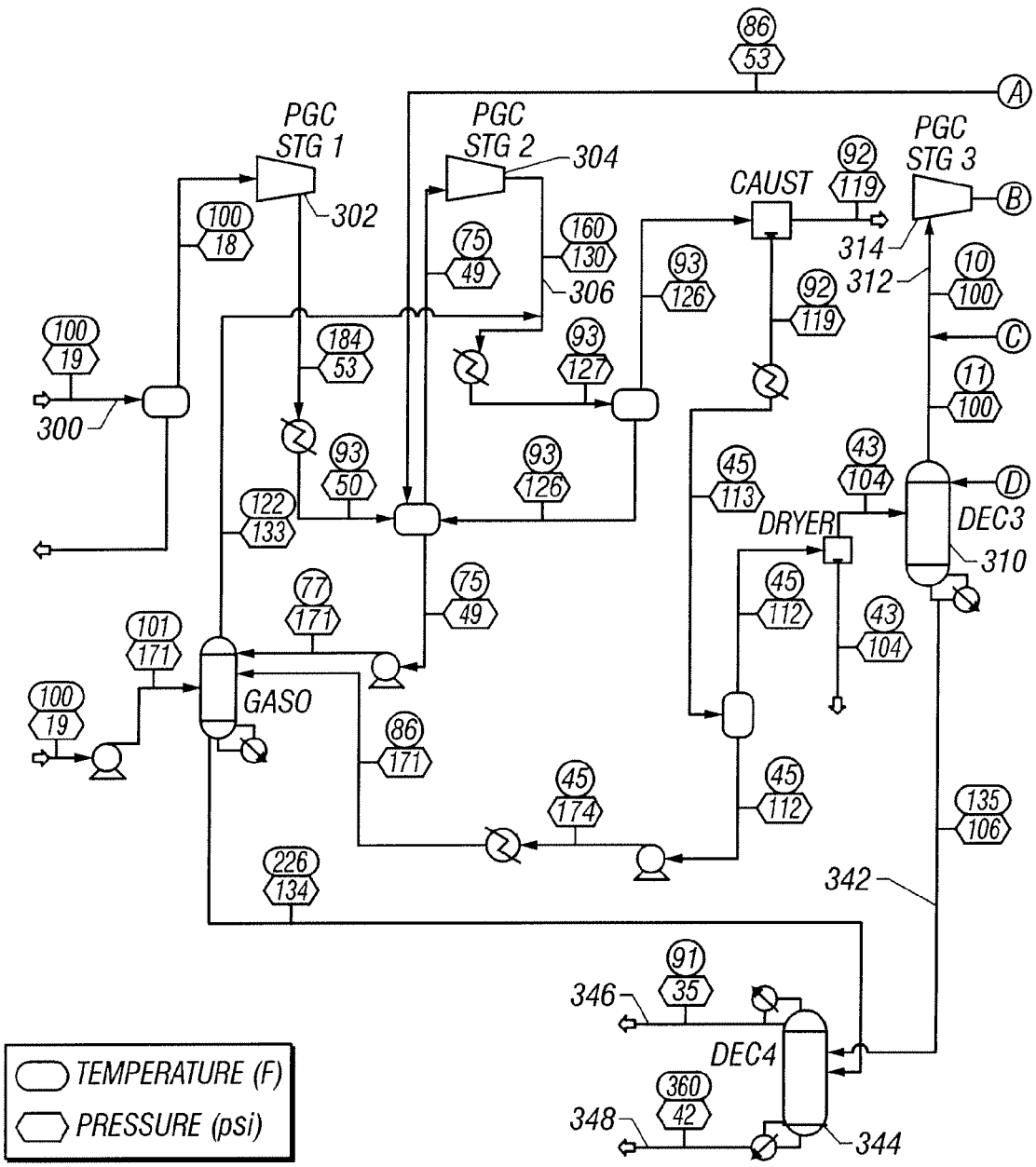
FIGS. 8A and 8B, taken together and referred to herein collectively as FIG. 8, are example simulation diagrams of the low pressure olefins recovery process of FIG. 3 showing pressure (oval/circular balloons) and temperature (hexagonal balloons) of selected streams, as discussed in Example 1 below.
Figure 8B:
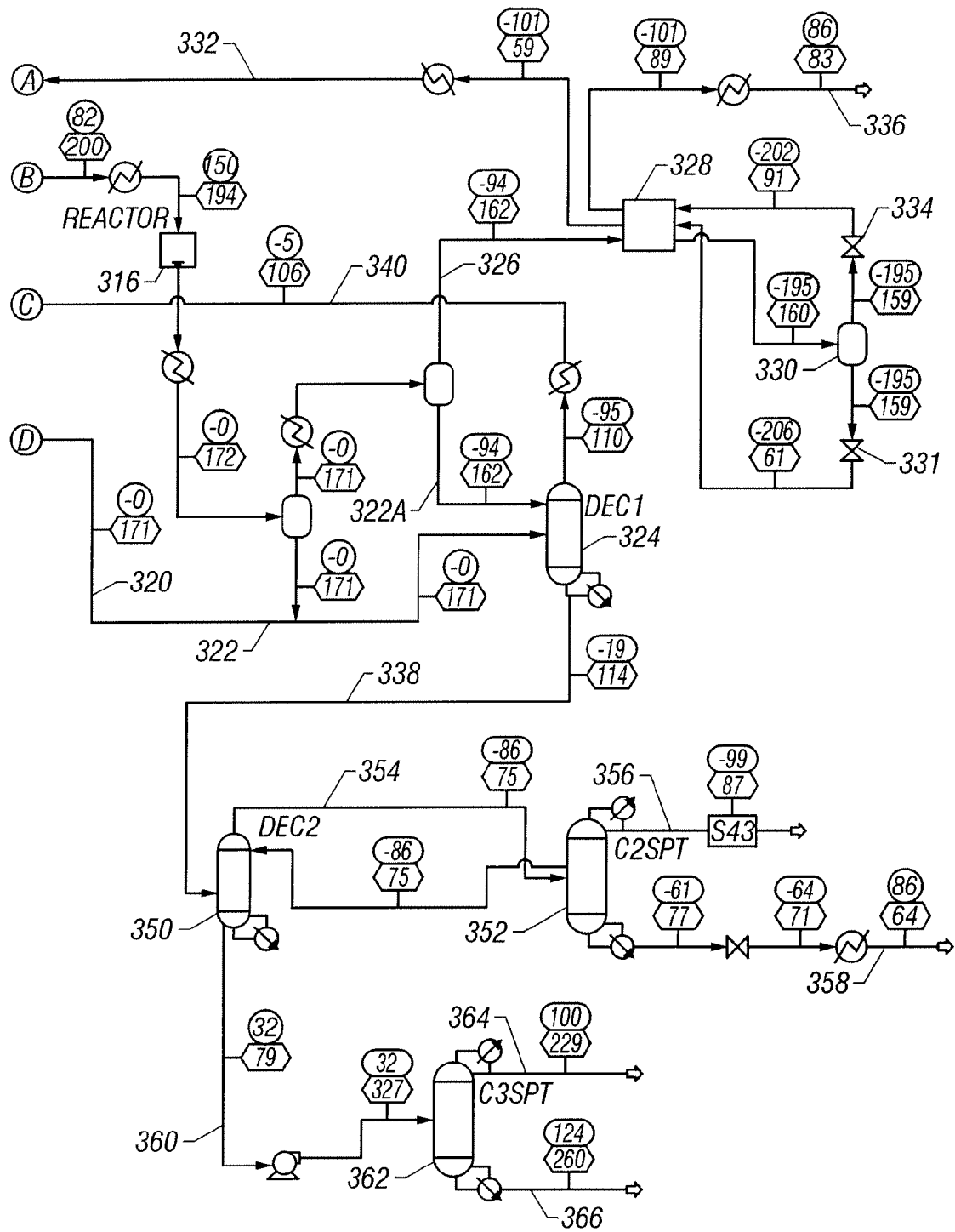

The embodiment of FIG. 3 was simulated on a commercial Aspen simulator using the simulation diagram seen in FIGS. 8A and 8B ("FIG. 8") with selected pressures (oval balloons) and temperatures (hexagonal balloons) as indicated. The feed is in the form of gas and liquid streams having the compositions summarized in Table 1.

TABLE 1

| Component | Vapor Feed (mol %) | Liquid Feed (mol %) |
| --- | --- | --- |
| $H_2$ | 6.4 | 0.0 |
| $N_2$ | 0.4 | 0.0 |
| $CO_2$ | 0.1 | 0.0 |
| $H_2S$ | 0.2 | 0.0 |
| $CH_4$ | 5.8 | 0.0 |
| $C_2H_4$ | 13.3 | 0.3 |
| $C_2H_6$ | 2.5 | 0.1 |
| $C_3H_6$ | 20.1 | 1.8 |
| $C_3H_8$ | 6.4 | 0.7 |
| 1,3-Butadiene | 0.1 | 0.0 |
| 1-Butene | 10.0 | 3.0 |
| i-Butane | 9.2 | 2.2 |
| n-Butane | 2.9 | 1.0 |
| $C_{5+}$ | 17.6 | 90.6 |
| $H_2O$ | 5.0 | 0.3 |
| Total Flow (kmol/hr) | 8200 | 1000 |

Three-stage process gas compression is used in a low-pressure recovery system. The front-end depropanizer 310 is operated at about 7 kg/cm2 (100 psia) riding on the third stage PGC 314 suction. The third stage PGC 314 discharge pressure is about 14 kg/cm2 (200 psia). The acetylene reactor is disposed downstream from the third stage PGC 314 to convert total acetylene to ethylene and ethane, and also to convert part of MAPD to propylene and propane. The acetylene reactor effluent is partially condensed against −20.8° C. (−5.4° F.) propylene refrigerant and part of the liquid provides reflux to the depropanizer 310. The process gas is further chilled against propylene and ethylene refrigerant to −71.7° C. (−97° F.). Condensed liquid is sent to the demethanizer 324 (sans condenser). Non-condensed vapor is chilled down to 126° C. through cold box exchanger 328. This partially condensed stream is sent to drum 330 to separate the Joule-Thompson recycle liquid from the tail gas vapor. The tail gas from the drum 330 overhead, consisting essentially of methane and lighter components but also containing some ethylene, is used as fuel gas after recovery of refrigeration in the cold box 328 exchangers. The Joule-Thompson recycle liquid from the bottom of the drum 330, consisting essentially of ethylene and some methane, is sent back to the suction of the second stage PGC 304 after recovering refrigeration through the cold box 328 exchangers. The demethanizer 310 is operated at about 7.7 kg/cm2 (110 psia), riding on the suction of the third stage PGC 314 to recover ethylene. The bottoms from the demethanizer 310 consist essentially of ethane, ethylene, propane and propylene and are sent to deethanizer 350, C2 splitter 352 and C3 splitter 362 to recover polymer grade ethylene and propylene. Ethane from the C2 splitter 352 bottoms can be combined with the tail gas 336 and eventually sent to the fuel gas system.

One advantage of this system is that low pressures are used. The maximum PGC discharge pressure is 14 kg/cm2 (200 psia), and no −100° C. (148° F.) refrigeration level is required, yet good ethylene recovery is achieved. To achieve this, a recycle stream is needed to provide refrigeration and minimize ethylene losses to tail gas. In effect, the ethylene loss to tail gas is controlled by the recycle separator drum 330 temperature. A lower temperature will reduce the ethylene loss in the tail gas 336, but will create a larger recycle, increasing the PGC power consumption as well as the ethylene and propylene refrigeration cycle power consumption. For example, the simulation diagram shown in FIG. 8 obtains ethylene recovery of about 98.6 percent with a power consumption of 43,369 kw for PGC's and refrigeration; but if ethylene recovery is pushed to 99.3 percent, then the PGC/refrigeration compression power consumption increases by 6.7 percent. Therefore, the tradeoff is between additional ethylene product gain versus the cost of the additional power consumption, and economic optimization depends on the ethylene value and power or fuel costs.

EXAMPLE 2

Figure 9A:
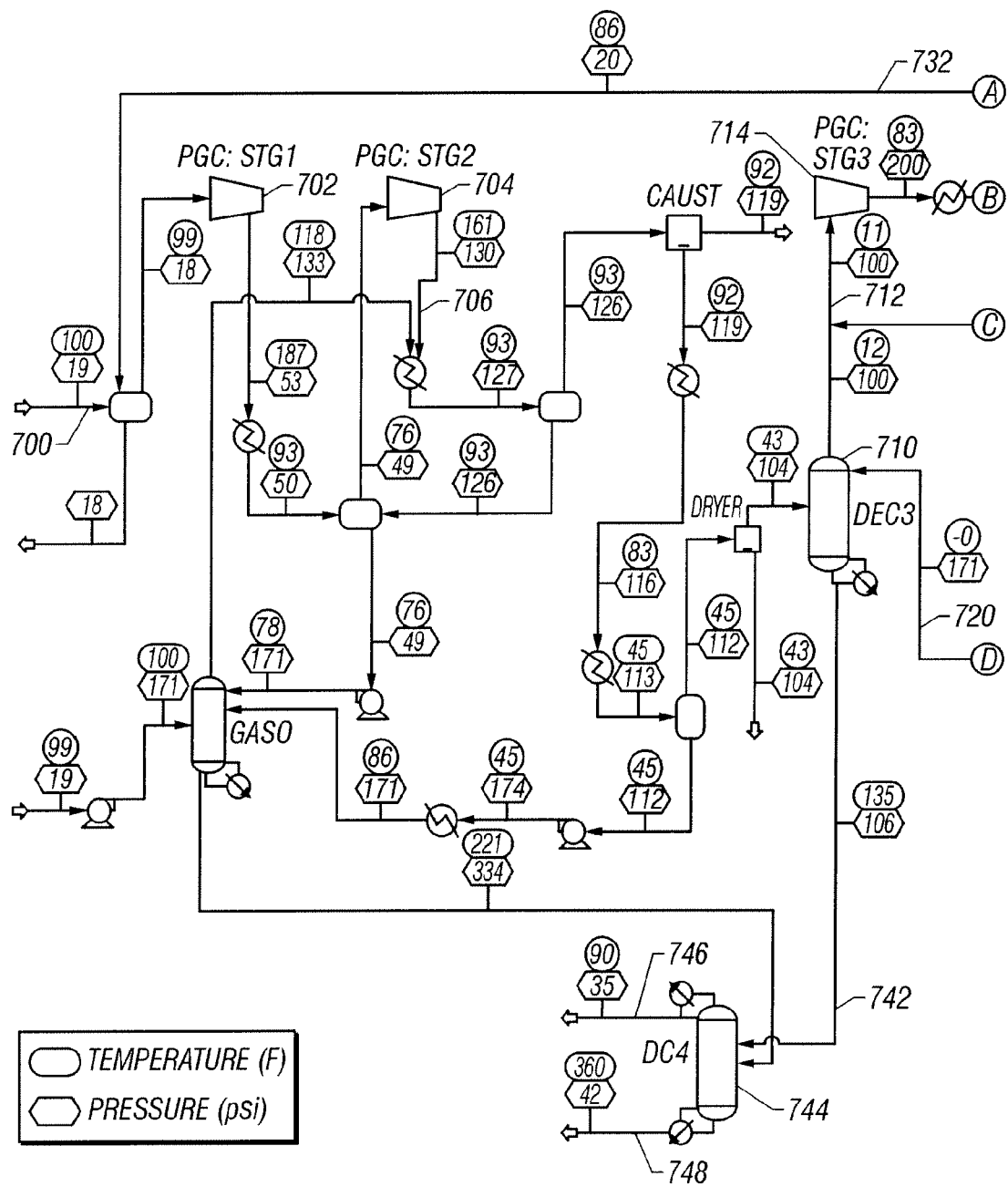
FIGS. 9A and 9B, taken together and referred to herein collectively as FIG. 9, are example simulation diagrams of the low pressure olefins recovery process of FIG. 7 showing pressure (oval/circular balloons) and temperature (hexagonal balloons) of selected streams, as discussed in Example 2 below.
Figure 9B:
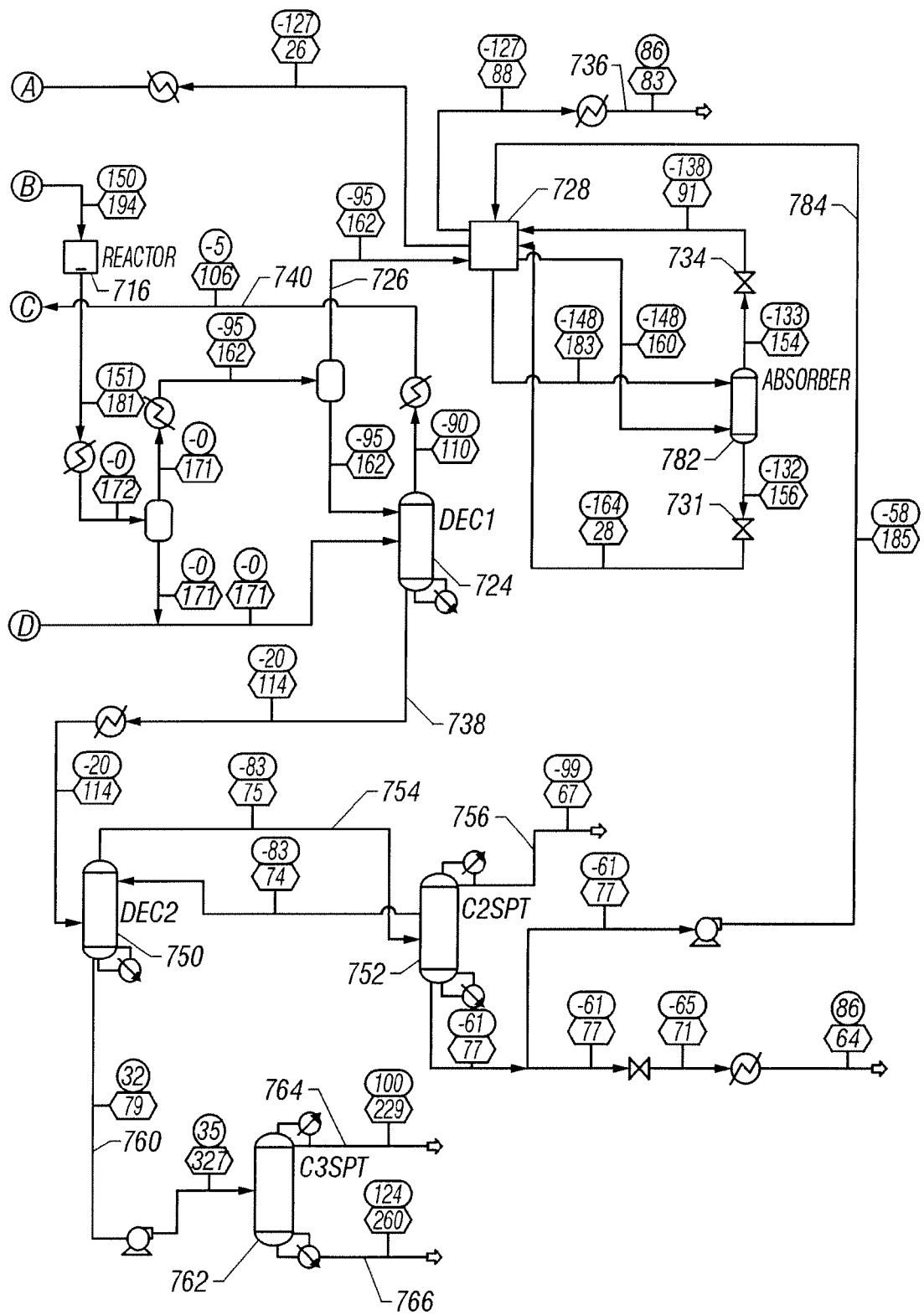

In this example, the embodiment of FIG. 7 was simulated as in Example 1 on a commercial Aspen simulator using the simulation diagram shown in FIGS. 9A and 9B ("FIG. 9") with selected pressures (oval balloons) and temperatures (hexagonal balloons). The absorber 782 is used in place of the separator drum 330. The partially condensed stream from the cold box 728 is sent to the absorber 782, which has just a few trays and no condenser or reboiler, so the additional capital cost compared to the separator drum 330 is minimal. The vapor stream 726 from the secondary demethanizer feed separator (a −70.6° C./−95.1° F. drum) is further chilled through the cold box 728 down to just −100° C. (−148° F.), compared to −126° C. (−195° F.) in the Example 1 scenario. The partially condensed stream is then fed to the bottom tray in the absorber 782. An ethane liquid stream 784 from the C2 splitter bottoms 758 is chilled to −100° C. (−148° F.) through an exchanger 786 (see FIG. 7) in the cold box 728. Mass transfer takes place in the absorber 782, wherein ethylene in the vapors in the partially condensed stream is absorbed in the liquid ethane. The overhead vapor (tail gas) stream 736 from the absorber 782, which is passed through cold box 728 for recovery of refrigeration, contains much less ethylene than in the FIG. 3 embodiment of Example 1. The bottoms liquid from the absorber 782 is expanded across valve 731, passed through cold box 728 for refrigeration recovery, and recycled via line 732 to the suction of the first stage PGC 702.

The use of the ethylene absorber 782 can obtain much higher ethylene recovery with a very small increase of power consumption. Compared to Example 1, for example, an ethylene recovery of 99.5 percent uses only 2.1 percent more power. In addition, this embodiment chills the process gas to only 100° C. (−148° F.), well above the nitrated-gum-formation temperature, thus enhancing the safety of the process Certain embodiments and features have been described using a set of numerical upper limits and a set of numerical lower limits. It should be appreciated that ranges from any lower limit to any upper limit are contemplated unless otherwise indicated. Certain lower limits, upper limits and ranges appear in one or more claims below.

All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

What is claimed is:

1. A process for recovering olefins from a feed stream, comprising:
   supplying the feed stream at a primary distillation pressure, including if required compressing the feed stream in a primary compression stage;
   distilling the feed stream at the primary distillation pressure in a primary distillation zone to obtain a primary overhead vapor stream enriched in ethylene and one or more ethylene-lean bottoms streams;
   chilling the primary overhead vapor stream at a pressure less than 24.5 kg/cm$^2$ in a first cooling stage to recover a first partial condensate stream and a first-stage vapor effluent;
   refluxing the primary distillation zone with at least a portion of the first partial condensate stream;
   further chilling the first-stage vapor effluent to recover at least a second partial condensate stream and a second-stage vapor effluent;
   feeding the at least second partial condensate stream and any remaining portion of the first partial condensate stream to a demethanizer to recover a methane-rich overhead stream and a bottoms stream essentially free of methane and lighter components;
   fractionating the bottoms streams from the primary distillation zone and the demethanizer into respective streams consisting essentially of hydrocarbons selected from the group consisting of ethylene, ethane, propylene, propane, C4's, C5+ and combinations thereof;
   further chilling the second-stage vapor effluent in a cold section and phase-separating the resulting mixed vapor-liquid stream in one or more stages to obtain additional condensate and a vapor tail gas stream essentially free of ethylene, wherein the additional condensate is vaporized to a relatively lower pressure to provide refrigeration for the condensation and to form a low pressure recycle vapor stream.

2. The process of claim 1 further comprising passing the feed stream in contact with a catalyst, adsorbent or combination thereof to remove at least one contaminant selected from the group consisting of acetylene, arsenic, mercury, carbonyl sulfide, nitrogen oxides, oxygen, and combinations thereof.

3. The process of claim 1 further comprising passing the primary overhead vapor stream in contact with a catalyst, adsorbent or combination thereof to remove at least one contaminant selected from the group consisting of acetylene, arsenic, mercury, carbonyl sulfide, nitrogen oxides, oxygen, and combinations thereof.

4. The process of claim 1 further comprising compressing the primary overhead vapor stream in a secondary compression stage to a discharge pressure effective to provide reflux for the primary distillation tower.

5. The process of claim 4 wherein the primary distillation pressure is from 7 to 21 kg/cm$^2$ and the discharge pressure from the secondary compression stage is greater than the primary distillation pressure and less than 28 kg/cm$^2$ (400 psia).

6. The process of claim 5 wherein the discharge pressure from the secondary compression stage is from 3.5 to 7 kg/cm$^2$ greater than the primary distillation pressure.

7. The process of claim 5 wherein the primary distillation pressure is from 7 to 11 kg/cm$^2$ and the discharge pressure from the secondary compression stage is from 10.5 to 17.5 kg/cm$^2$.

8. The process of claim 4, further comprising recycling the overhead stream from the demethanizer into the primary overhead vapor stream upstream from the secondary compression stage.

9. The process of claim 8, wherein the demethanizer consists essentially of an unrefluxed stripper column.

10. The process of claim 1, wherein the primary distillation zone comprises a depropanizer and the process further comprises fractionating the bottoms stream from the depropanizer in a debutanizer to obtain respective streams consisting essentially of C4's and C5's and heavier hydrocarbons, and fractionating the bottoms stream from the demethanizer in a deethanizer, a C2 splitter and a C3 splitter to obtain respective streams consisting essentially of ethylene, ethane, propylene and propane.

11. The process of claim 10, comprising exporting a portion of an overhead stream from the deethanizer.

12. The process of claim 10, comprising exporting a portion of the first-stage vapor effluent.

13. The process of claim 10, wherein the deethanizer is refluxed with a side draw from the C2 splitter.

* * * * *